United States Patent [19]

Jefferies

[11] Patent Number: 4,472,840
[45] Date of Patent: Sep. 25, 1984

[54] METHOD OF INDUCING OSSEOUS FORMATION BY IMPLANTING BONE GRAFT MATERIAL

[76] Inventor: Steven R. Jefferies, 5802 Leith Walk, Baltimore, Md. 21239

[21] Appl. No.: 430,597

[22] Filed: Sep. 30, 1982

Related U.S. Application Data

[62] Division of Ser. No. 304,367, Sep. 21, 1981, Pat. No. 4,394,370.

[51] Int. Cl.$^3$ .......................... A61F 1/00; A61F 5/04
[52] U.S. Cl. ................................... 3/1.9; 128/92 G; 128/92 C; 3/1
[58] Field of Search ................... 128/92 C, 92 G, 325; 3/1, 1.9; 424/15, 14; 106/161, 122

[56] References Cited

U.S. PATENT DOCUMENTS 3,551,560  12/1970  Thiele .......................................... 3/1
4,314,380  2/1982  Miyata et al. ............................. 3/1.9
4,347,234  8/1982  Wahlig et al. ............................ 3/1.9

FOREIGN PATENT DOCUMENTS 30583  6/1981  European Pat. Off. ................. 3/1.9

OTHER PUBLICATIONS

Urist, Proc. Natl. Acad. Sci., USA 76: 1828–1932, 1979.

Primary Examiner—Richard J. Apley
Assistant Examiner—David J. Isabella
Attorney, Agent, or Firm—Cushman, Darby & Cushman

[57] ABSTRACT

Complexes of reconstituted collagen and demineralized bone particles or reconstituted collagen and a solubilized bone morphogenetic protein fabricated in a sponge suitable for in vivo implantation in osseous defects are disclosed. Both demineralized bone particles (DBP) and bone morphogenetic protein have demonstrated the ability to induce the formation of osseous tissue in animal and human experiments. Reconstituted collagen conjugate is highly biocapatible and can be fabricated in a variety of configurations, especially as a sponge. This material can be used as a grafting implant in plastic and reconstructive surgery, periodontal bone grafting, and in endodontic procedures. Structural durability is enhanced by cross-linking with glutaraldehyde which is also used to sterilize and disinfect the collagen conjugate prior to implantation.

8 Claims, No Drawings

METHOD OF INDUCING OSSEOUS FORMATION BY IMPLANTING BONE GRAFT MATERIAL

CROSS-REFERENCE TO RELATED APPLICATIONS

This application is a division of my earlier copending application Ser. No. 304,367 filed Sept. 21, 1981, now U.S. Pat. No. 4,394,370 issued July 19, 1982.

BACKGROUND OF THE INVENTION

This invention relates to a biocompatible, osteogenic, collagen conjugate material, particularly in the form of a sponge, and to a process for making this material. While individual components of this system are known in the art and in the related literature, described herein is a novel composite material, specifically designed to induce osteogenesis within its porous structure, completely biocompatible and non-inflammatory, and ultimately resorbed and replaced by calcified, hard tissue.

Collagen was chosen as the binding matrix and main structural component of the novel graft material herein described for several reasons:

(1) Reconstituted collagen has demonstrated excellent histocapatibility without antibody formation or graft rejection in numerous in vivo implantation studies.

(2) Reconstituted collagen can be fabricated into porous sponge-like structures which allow unimpeded cellular ingrowth.

(3) Collagen is the natural biomaterial which constitutes from 50 to 70% by weight of the bone organic matrix.

(4) Reconstituted collagen has demonstrated the ability to bind both large and small molecular weight macromolecules and complexation with collagen protects these macromolecules from denaturation due to environmental influences, such as glutaraldehyde cross-linking or the effect of other chemical agents; see M. Chvapil et al, International Review of Connective Tissue Research, Vol. 6, (1973), pp. 1–55; S. R. Jefferies et al, Journal of Biomedical Materials Research, Vol. 12 (1978), pp. 491–503; and U.S. Pat. No. 3,843,446.

Sterile collagen products having a felt or fleece-like structure with open, communicating voids between the fibers and used as an absorbent in wounds and bone cavities are described in U.S. Pat. No. 4,066,083.

In 1931, Huggins (Arch. Surg., 22:377–408) reported that proliferating mucosa of kidney, ureter, or bladder induced bone formation when implanted in connective tissue. This was the first reported experimental model of induced ectopic osteogenesis. More recently, Urist (Science, 150: 893–899, 1965) and Reddi et al (Proc. Natl. Acad. Sci. USA, 69: 1601–1605, 1972) demonstrated that osteogenesis could also be induced by the devitalized, demineralized matrix of bone or dentin. It has been shown that physical factors, including surface charge and geometry of the matrix, are involved, Reddi et al (Proc. Natl. Acad. Sci. USA, 69: 1601–1605, 1972). There is evidence that a soluble factor from demineralized bone, bone morphogenetic protein, is osteo-inductive; see Urist et al, Proc. Natl. Acad. Sci. USA, 76: 1828–1932, 1979.

In 1899, Senn showed healing of experimental canine calverial defects and of human tibial and femoral defects with decalcified ovine bone. Others have shown bone formation in periapical areas in dogs and monkeys and in skull defects in rats after implantation of demineralized bone by itself. The osteogenic potential of demineralized bone powder has been demonstrated in cranial osseous defects in rats. More recently, Mulliken reported on the use of demineralized bone segments, chips, and powder for reconstruction of craniofacial defents in rats and humans; see Mulliken et al, Plast. Reconstr. Surg., 65: 553—559, 1980 and Glowacki et al, Lancet, 2 May, 1981, 963–966.

Histomorphometric evaluation of osteogenesis induced by equal masses of demineralized bone powders of various particle sizes, ranging from less than 75 millimicrons to greater than 450 millimicrons, has revealed that smaller particles induced more bone per field, that is the ratio of bone area to implant area, than did larger particles. It has also been noted in the literature that large blocks of demineralized cortical bone induce only a thin layer of new bone on their surfaces. Osteogenesis proceeds more slowly in response to blocks than to powders.

Although blocks, chips, and powders of demineralized bone by itself may be useful for repair of bony defects, a more defined, better designed material is needed to improve the clinical usefulness of induced osteogenesis. Greater control is required over the chemical composition of the graft material than previously accomplished. Banked bone taken from cadavers for demineralization (allogenic bone) must be harvested under rigid standards and conditions to prevent possible immunologic complications or possible transmission of viral or bacterial pathogens. Gamma radiation, one method for sterilization of demineralized bone, may alter the physio-chemical properties critical for bone induction. It is recognized that irradiation of demineralized bone powder before implantation weakens the osteogenic response by 20%.

SUMMARY OF THE INVENTION

I have found that complexes of reconstituted collagen with demineralized bone particles or complexes of reconstituted collagen and solubilized bone morphogenic protein, optionally with glutaraldehyde as a cross-linker, when fabricated into sponges or like forms and implanted in vivo in osseous defects induces the formation of osseous tissue in the animal in which it is implanted. Such complexes are conveniently fashioned into a suitable form for application/implantation including thin membranes, gels or preferably in a sponge-like configuration. The complexes of my invention are suitable for many applications including grafting implants in plastic and reconstructive surgery, periodontal bone grafting, and in endodontic procedures.

Several properties of demineralized bone and its ability to induce osteogenesis are apparent: particles of demineralized bone appear to induce greater quantities of new bone than do blocks or chips. Particles of smaller dimensions induced more bone, expressed as bone area per implant area, than did larger particles of demineralized bone. Large sections of demineralized bone appear to induce osteogenesis only at their surface, not deep within the graft itself. Gamma radiation as used in sterilization appears to decrease osteogenic ability of demineralized bone material, especially irradiation levels above 1 Mrad of Cobalt 60. A glycoprotein, bone morphogenetic protein (BMP), has been characterized and is reported to have induced new bone formation in rats. BMP's action does not appear to be species-specific; rabbit BMP has induced new bone formation in rats.

Microparticulate demineralized bone can be complexed with collagen dispersions and case into microporous ϟponges for implantation. Collagen-BMP conjugate sponges can be prepared in a similar fashion. These composite materials have several advantages over banked, demineralized allogenic bone obtained from human cadavers. The novel complexes of my invention combine the osteogenic potential of demineralized bone with the excellent biocompatibility of reconstituted collagen. Collagen, a component of bone matrix, has been shown to increase fibroblast migration and proliferation; see Ehrmann et al, J. Nat. Can. Inst., 16: 1475-1390 (1956), and to also increase the rate and extent of cell attachment; see also Klebe, Nature, 250: 248-251 (1974).

By the use of demineralized bone powder or bone morphogenic protein as a controlled spore material to allow cellular ingrowth, osteogenic cells can proliferate throughout the graft material, allowing bony union of the graft and bone formation uniformly within the graft. Greater control over the chemical composition of the graft material is now possible, thus reducing the possibility of graft-host rejection due to histo-incompatibility or inflammation. The Collagen-DBP and Collagen-BMP conjugates of my invention increase the available surface area of the immobilized powder or protein, thus increasing the extent of bone induction into the implanted mass. Collagen-DBP and Collagen-BMP conjugates confer protection to the physical-chemical properties of the non-collagen proteins in the conjugate during sterilization by chemical means or irradiation.

Proportions of the BMP and/or DBP may be adjusted within reasonably wide ranges depending upon the properties desired and the clinical applications required. A majority, i.e., more than 50 weight percent of the conjugate material is collagen. Preferably the BMP, DBP or their mixture are present, in sum, to the extent of from about 5 to about 35 weight percent, most preferably from about 10 to about 20 weight percent, with from about 1 to about 5 weight percent glutaraldehyde, when present, balance collagen. A preferred formulation includes 10 to 20 weight percent DBP or BMP, about 1 weight percent glutaraldehyde, balance reconstituted collagen.

The invention will now be further described with reference to the following examples, considered illustrative but not limiting of the invention. Unless otherwise indicated, all parts and percentages are by weight.

EXAMPLE I

A. Preparation of Demineralized Bone Particles—Allogenic bone material was obtained from human cadavers from an organ bank. Bones were cleaned and extracted with absolute ethanol followed by anhydrous ethyl ether. The bones were then pulverized in a Spex liquid nitrogen impacting mill and sieved to particle size of less than 75 millimicrons ($\mu$m) to yield bone powder particles.

Demineralized bone powder (DBP) was prepared by extracting the previously prepared bone powder particles with 0.5M HCl (25 Meq/gm bone) for 3 hours at room temperature followed by six washes in sterile distilled water to remove all acids and calcium, followed by four sequential 60-minute washes in absolute ethanol and anhydrous ether.

B. Complexation of DBP with Reconstituted Collagen—Collagen-DBP conjugates were prepared as follows: 10 grams of pulverized, lyophilized, microcrystalline collagen (Avitene, Avicon, Inc., Fort Worth, Tex.) were dialyzed against sterile distilled water for 24 hours to remove the hydrochloric acid salt used in the collagen's preparation. The collagen was then dispersed in 500 milliliters of 0.05M acetic acid (pH 3.2) by stirring in a refrigerated homogenizer. 1 (one) gram of DBP was slowly added to the collagen dispersion. This resulted in approximately 10% DBP in the collagen.

Glutaraldehyde cross-linking, an optional but preferred procedure which increases the mechanical strength of the conjugate collagen sponge, can be performed during the homogenization step after the addition of DBP. 19.2 milliliters of 25%, biological grade glutaraldehyde (Eastman Chemical Co.) were slowly added to the collagen dispersion to create a final concentration of 1% glutaraldehyde. Alternatively, the glutaraldehyde cross-linking step may be performed after fabrication of the lyophilized collagen sponge, in the manner described below.

100 milliliters of the Collagen-DBP dispersion (collagen-particle composite material) prepared as described above of approximately 2.2% solids by weight (2% collagen, 0.2% DBP) were then placed in an aluminum container measuring 5 cm×5 cm×5 cm. The container was placed on the −50° C. shelf of a lyophilizer and the contents of the aluminum cube were frozen thereon. The frozen dispersion was then quickly removed from the container and placed directly in the vacuum chamber of the lyophilizer. The condenser coils were cooled to −150° C. with liquid nitrogen and the vacuum was maintained at approximately 60 mtorr with the use of a pump (Model D150, Precision Scientific, Chicago, Ill.). The specimen was maintained at approximately −70° C. during the freeze drying process. The dried specimen was a white, semi-rigid foam.

If the Collagen-DBP conjugate has not been cross-linked earlier in this procedure, the sponge can be cross-linked in 1% glutaraldehyde (adjusted to pH 7.0 with sodium phosphate buffer) for 15 minutes at 20° C. under mild stirring. The final concentration of phosphate buffer in the cross-linking bath was 0.01M. Following cross-linking, the sponge is removed and placed in a stirred bath of 0.005M glycine in sterile distilled water for 30 minutes. The sponge is then washed with 10 batch contacts of sterile distilled water and finally stored in a sealed, sterile container of sterile normal saline.

EXAMPLE II

A procedure described by Urist et al (Proc. Natl. Acad. Sci. USA, 76 1828-1932, 1979), the disclosure of which is incorporated herein by reference, for isolation of a solubilized bone morphogenetic protein (BMP), which can induce a osteogenesis in vivo, was modified for the isolation of BMP to produce Collagen-BMP bone graft sponges.

Allogenic cortical bone (100 grams) was demineralized in 0.5M HCl at 4° C. for 24 hours. The demineralized bone was then washed twice in sterile distilled water and then lyophilized. The lyophilized matrix was then sequentially extracted three times with 8M LiCl to decrease the content of lipid, proteoglycans, and sialoproteins and to convert the bone collagen to insoluble bone matrix gelatin.

The bone matrix gelatin was incubated for 24 hours at 37° C. at pH 7.2 in a 0.00054% purified bacterial collagenase (Worthington Bichemical Corp.) in Hanks' solution containing 25 mM Tris, 300 mM $CaCl_2$, 3 mM NaN₂, and adjusted to a pH of 7.2 with 0.1M HCl. The pH was adjusted to 7.2 every two hours for the first eight hours. After 24 hours, the total digest was centrifuged at 40,000×G for 15 minutes. The resulting pellet of insoluble collagenase-resistant material was discarded. The supernatant, a clear solution, was then dialyzed in cellulose acetate membrane, 0.30 μm pore size, against sterile distilled water for 24 hours at 4° C. The dialysate, containing the non-dialyzable substances, was retained and used for complexation with reconstituted collagen as described above.

The complexation of BMP with reconstituted collagen was identical with the procedure followed in Example I except that BMP solution was added instead of DBP particles. Alternatively, one may mix the BMP and DBP sources in complexing with the reconstituted collagen.

EXAMPLE III

An additional modification of the Collagen-DBP and Collagen-BMP conjugates can be accomplished through the additional binding of auxillary macromolecules in order to modify or accelerate the osteogenic properties of the conjugate materials. For example, the complexation of bovine intestinal alkaline phosphatase, at concentrations of 15 mg per gram of Collagen dispersion (either Collagen-DBP or Collagen-BMP dispersions), acts to eliminate all inflammatory responses to the graft material, accelerates the formation of osteoid in the graft material, and slows resorption of the graft enabling it to be more completely corticalized.

What is claimed is:

1. A method of grafting bone in an animal requiring a bone implant comprising introducing into said animal a bone graft material adapted to induce the formation of osseous tissue in said animal, said bone graft material consisting essentially of a collagen conjugate containing:
   from about 65 to about 95 weight percent reconstituted collagen having dispersed substantially uniformly therein
   from about 35 to about 5 weight percent of a member selected from the group consisting of (a) demineralized bone particles, (b) solubilized bone morphogenic protein, and (c) mixtures of demineralized bone particles and solubilized bone morphogenic protein.

2. The method of claim 1 wherein the bone graft material contains about 80 to about 90% reconstituted collagen and the amount of one of (a), (b) and (c) is about 20 to about 10%.

3. The method of claim 1 wherein the glutaraldehyde is present in an amount of about 1 to about 5 weight percent.

4. The method of claim 1 wherein the reconstituted collagen is complexed with alkaline phosphatase.

5. A method of grafting bone in an animal requiring a biocompatible bone graft implant, said method comprising introducing a biocompatible bone graft material composed of a collagen conjugate capable of inducing the formation of osseous tissue in the animal in which it is implanted, said bone graft material consisting essentially of, in weight percent:
   (i) from about 65 to about 95% reconstituted collagen complexed with alkaline phosphatase, the collagen having dispersed substantially uniformly therein
   (ii) from about 35 to about 5% of demineralized bone particles, and
   (iii) a cross-linking amount of glutaraldehyde to confer structural integrity to the bone graft material,
   said bone graft material being substantially noninflammatory and biocompatible with the tissue in the animal in which it is implanted and adapted to induce osteogenesis in said animal.

6. A method of grafting bone in an animal requiring a biocompatible bone graft implant, said method comprising introducing into said animal a biocompatible bone graft material composed of a collagen conjugate capable of inducing the formation of osseous tissue in the animal in which it is implanted, said bone graft material consisting essentially of, in weight percent:
   (i) from about 65 to about 95% reconstituted collagen complexed with alkaline phosphatase, the collagen having dispersed substantially uniformly therein
   (ii) from about 35 to about 5% of solubilized bone morphogenic protein, and
   (iii) a cross-linking amount of glutaraldehyde to confer structural integrity to the bone graft material,
   said bone graft material being substantially noninflammatory and biocompatible with the tissue in the animal in which it is implanted and adapted to induce osteogenesis in said animal.

7. The method of claim 5 wherein the amount of glutaraldehyde is from about 1 to about 5%.

8. The method of claim 6 wherein the amount of glutaraldehyde is from about 1 to about 5%.

* * * * *